United States Patent [19]

Klaubert et al.

[11] Patent Number: 4,504,660

[45] Date of Patent: Mar. 12, 1985

[54] PROCESS FOR THE PRODUCTION OF 2,6-DIAMINOBENZONITRILE DERIVATIVES

[75] Inventors: Dieter H. Klaubert, Perkiomenville; Stanley C. Bell, Narberth, both of Pa.

[73] Assignee: American Home Products Corporation, New York, N.Y.

[21] Appl. No.: 395,520

[22] Filed: Jul. 6, 1982

[51] Int. Cl.³ .................. C07C 121/52; C07D 207/04
[52] U.S. Cl. .................. 544/163; 544/395; 260/465 E; 546/230; 548/577
[58] Field of Search .................. 260/465 E; 544/163, 544/395; 546/230; 548/577

[56] References Cited

U.S. PATENT DOCUMENTS

| | | | |
|---|---|---|---|
| 4,013,647 | 3/1977 | Sellstedt et al. | 260/247.2 A |
| 4,054,591 | 10/1977 | Klaubert et al. | 260/465 D |
| 4,137,325 | 1/1979 | Sellstedt et al. | 424/311 |
| 4,359,428 | 11/1982 | Jacobs et al. | 260/465 E |

OTHER PUBLICATIONS

Klaubert et al., J. Med. Chem. 24, 742, (1981).
DeVries et al., J. Med. Chem. 19, 946, (1976).
Williams et al., J. Org. Chem. 42, 3414, (1977).
Beck, Tetrahydron 34, 2057, (1978).

*Primary Examiner*—Nicky Chan
*Attorney, Agent, or Firm*—Richard K. Jackson

[57] ABSTRACT

2,6-Diaminobenzonitriles, useful in the production of N-(2-cyano-3-substituted or unsubstituted aminophenyl)oxamate and N-(2-cyano-3-substituted or unsubstituted amino-phenyl)tetrazole-5-carboxamide antiallergy and antisecretory agents, are prepared by sequential displacement of the fluoro substituents from 2,6-difluorobenzonitrile with the appropriately substituted amine.

1 Claim, No Drawings

PROCESS FOR THE PRODUCTION OF 2,6-DIAMINOBENZONITRILE DERIVATIVES

BACKGROUND OF THE INVENTION

A series of 3-substituted or unsubstituted amino-2-cyano-oxanilic acids, esters and salts were recently found to be excellent antiallergy agents and/or antisecretory agents. (U.S. Pat. Nos. 4,013,647; 4,054,591 and 4,137,325). These compounds were produced by displacement of a nitro group from 2,6-dinitrobenzonitrile with a desired amine followed by reduction of the remaining nitro group and reaction with an alkyloxalyl halide with subsequent workup. The dinitrobenzonitrile precursor is conventionally prepared by reaction of copper cyanide with 1-chloro-2,6-dinitrobenzene, the latter compound being a toxic, carcinogenic, skin irritant. Handling of 1-chloro-2,6-dinitrobenzene requires special techniques, and equipment which make its use very undesireable, especially if large quantities of the compound are to be employed in scaled up production of the 2,6-dinitrobenzonitrile. Thus, a method for introducing amine substituents ortho to a nitrile substituent of benzene, which avoids the use of 1-chloro-2,6-dinitrobenzene would be of great advantage in the production of the known antiallergy-antisecretory compounds.

DESCRIPTION OF THE INVENTION

In accordance with this invention there is provided a process for the production of 2,6-diaminobenzonitriles of the formula:

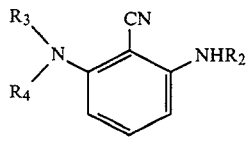

I wherein
$R_2$ is hydrogen or methyl and
$R_3$ and $R_4$ are, independently, hydrogen, alkyl of 1 to 6 carbon atoms, aralkyl of 7 to 12 carbon atoms, cycloalkyl of 5 to 8 carbon atoms or aryl of 6 to 12 carbon atoms
or
$R_3$ and $R_4$, taken with the nitrogen atom to which they are attached represent 1-pyrrolidinyl, 1-piperidinyl, 1-piperazinyl, 4-methyl-1-piperazinyl or 4-morpholinyl,
which comprises sequentially displacing the two fluoro substituents of 2,6-difluorobenzonitrile with the amines $R_2NH_2$ and $NHR_3R_4$.

The aromatic nucleophilic displacement of two fluoro substituents ortho to an activating nitrile function on benzene proceeds in a manner similar to the more conventional displacement of nitro groups in that the first fluoro substituent is more readily displaced than the second. Thus, the initial displacement will proceed more facilely than the second, the latter requiring the application of elevated temperature and, frequently, pressure. The reaction stages are remarkably distinct in that a large stoichiometric excess of amine may be employed in the first displacement without effecting double displacement to a diamine product. Reaction conditions to achieve stepwise displacement of the two fluoro substituents will vary with the amine reactant, but appropriate time-temperature-pressure parameters are readily accertainable and optimized by observing the results of a few runs with thin layer liquid chromatography.

With the majority of amine reactants, the first displacement occurs readily at room temperature. The second displacement requires more strenuous conditions of temperature, time and pressure. In general, with all of the amine reactants, the first displacement will occur within the temperature range of about 0° C. to about 75° C. while the second displacement is effected at a temperature of about 75° C. to about 200° C. An applied pressure from atmospheric to about 200 psi guage may be employed during either displacement. Obviously, where the reaction temperature is above the boiling point of the amine reactant or the solvent employed, autogenous pressure is a minimal pressure requirement. Ammonia is an anamolous example of the amine reactants in that it requires much more drastic reaction conditions than primary or secondary amine reactants.

The salt equivalents of ammonia or substituted amines may be used to generate the desired reactant in situ. Thus, the carbonates, acetates, etc. are applicable sources of amines for use in the process. Similarly, formamide and N-substituted formamides which decompose at elevated temperatures are sources for the amine reactant and may be used alone or in conjunction with the free amines or their salt equivalents. Throughout this disclosure and the appended claims, reference to an amine reactant is understood to embrace the equivalent salt or formamide.

The first aromatic nucleophilic displacement step, as an additional process aspect of the invention is defined as a process for the production of a 2-amino-6-fluoro-benzonitrile of the formula:

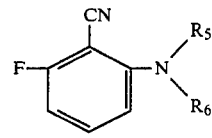

wherein
$R_5$ and $R_6$ are, independently, hydrogen, alkyl of 1 to 6 carbon atoms, aralkyl of 7 to 12 carbon atoms, cycloalkyl of 5 to 8 carbon atoms or aryl of 6 to 12 carbon atoms
or
$R_5$ and $R_6$, taken with the nitrogen atom to which they are attached represent 1-pyrrolidinyl, 1-piperidinyl, 1-piperazinyl, 4-methyl-1-piperazinyl or 4-morpholinyl,
which comprises displacing a fluoro substituent from 2,6-difluorobenzonitrile with $NHR_5R_6$.

The products of the initial fluoro group displacement represent the compound aspect of this invention. They are represented by the structural formula:

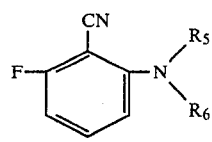

wherein
$R_5$ and $R_6$ are, independently, hydrogen, alkyl of 1 to 6 carbon atoms, aralkyl of 7 to 12 carbon atoms, cycloalkyl of 5 to 8 carbon atoms or aryl of 6 to 12 carbon atoms, or R$_5$ and R$_6$, taken with the nitrogen atom to which they are attached represent 1-pyrrolidinyl, 1-piperidinyl, 1-piperazinyl, 4-methyl-1-piperazinyl, or 4-morpholinyl.

As may be seen from the structural formula of the product of the initial fluoro substituent displacement, either amine appearing in the final product may be introduced first and the other amine introduced subsequently.

The process of this invention includes as a distinct embodiment, the second fluoro group displacement for production of the desired 2,6-diaminobenzonitrile compounds, which process may be expressed as a process for production of compounds of formula I, supra, which comprises displacing the fluoro substituent from a 2-amino-6-fluorobenzonitrile derivative of the formula:

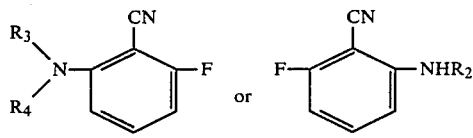

with the amines H$_2$NR$_2$ or NHR$_3$R$_4$, respectively.

The 2,6-diaminobenzonitrile products of the processes of this invention are intermediates for use in the production of antiallergy agents and antisecretory agents such as are disclosed in J.Med.Chem., 24 742–748, June 1981 and U.S. Pat. Nos. 4,013,647, 4,054,591 and 4,137,325. Acylation of the primary or secondary amine substituent(s) of the products of the process of this invention with an alkyloxalylhalide or a tetrazole-5-carbonyl halide is accomplished by the procedures set forth in those references, which disclosure is incorporated herein by reference.

The following examples representatively illustrate the processes of this invention as well as the production of the intermediate 2-amino-6-fluorobenzonitriles.

EXAMPLE 1

2-Amino-6-fluorobenzonitrile 2,6-Difluorobenzonitrile, 19 g (0.14 mol) in 200 ml of ethanol saturated with NH$_3$ at 0° C. is heated in a sealed vessel at 140° C. for 6 hrs. The mixture is evaporated to dryness, water is added and the product is collected and recrystallized from benzene, m.p. 128°–130° C.

EXAMPLE 2

2-Amino-6-fluorobenzonitrile

The above product is prepared by heating a five molar excess of (NH$_4$)$_2$CO$_3$ and 2,6-difluorobenzonitrile in formamide at 110° C. for 2 hrs. Alternatively, NH$_4$OAc in formamide at 130° C. for 4 hrs also gives the same product.

EXAMPLE 3

2-Amino-6-methylaminobenzonitrile

2-Amino-6-fluorobenzonitrile (200 mg) is heated in a sealed vessel in ethanol saturated with methylamine gas at 140° C. for 4 hrs. The solvent is evaporated, water is added and the product is extracted into methylene chloride. Evaporation of the solvent gives the title compound as an oil, (200 mg) which is converted to the crystalline hydrochloride with i-propanolic HCl-diethyl ether, m.p. 214°–216° C. (dec).

EXAMPLE 4

2-Amino-6-methylaminobenzonitrile

The title compound is prepared by heating a 10 molar excess of methylammonium acetate and 2-amino-6-fluorobenzonitrile in N-methyl formamide at 140° C. for 5 hrs.

EXAMPLE 5

2-Fluoro-6-methylaminobenzonitrile 2,6-Difluorobenzonitrile, 2.78 g (20 mmol) and 5 ml (60 mmol) of 40% aqueous methylamine in 50 ml DMF is stirred at room temperature for 1 hr., poured into water and the product is collected, 2.4 g m.p. 130°–132° C.

Analysis for: C$_8$H$_7$N$_2$F, Calculated: C, 63.99; H, 4.70; N, 18.66, Found: C, 64.09; H, 4.89; N, 18.21.

EXAMPLE 6

2-Fluoro-6-(4-methylpiperazinyl)benzonitrile 2,6-Difluorobenzonitrile is reacted with N-methyl piperazine following the procedure of Example 5. The reaction mixture is extracted with methylene chloride after addition of water. The methylene chloride is extracted with dilute HCl which is basified and extracted with methylene chloride. The resulting crude oil after evaporation is taken in ethanol and i-PrOH-HCl is added to give the title compound as the hydrochloride salt, 1.4 g m.p. 245°–247° C.

Analysis for: C$_{12}$H$_{14}$N$_3$F HCl, Calculated: C, 56.36; H, 5.91; N, 16.43, Found: C, 56.67; H, 6.18; N, 16.21.

EXAMPLE 7

2-Fluoro-6-anilinobenzonitrile

A mixture of 2.8 g (20 mmol) of 2,6-difluorobenzonitrile in 20 ml of aniline is refluxed for 6 hrs. The mixture is poured into diluted HCl and the acid is extracted with methylene chloride. Evaporation gives the crude product which is chromatographed on silica gel (50% hexane—CH$_2$Cl$_2$) to give the title compound, m.p. 97°–99° C.

Analysis for: C$_{13}$H$_9$N$_2$F, Calculated: C, 73.57; H, 4.27; N, 13.20, Found: C, 72.77; H, 4.72; N, 12.89.

What is claimed is:

1. A process for production of a compound of the formula:

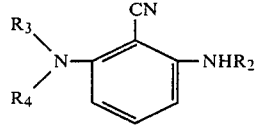

wherein

R$_2$ is hydrogen or methyl and

R$_3$ and R$_4$ are, independently, hydrogen, alkyl of 1 to 6 carbon atoms, aralkyl of 7 to 12 carbon atoms, cycloalkyl of 5 to 8 carbon atoms or aryl of 6 to 12 carbon atoms, or R$_3$ and R$_4$, taken with the nitrogen atom to which they are attached represent 1-pyrrolidinyl, 1-piperidinyl, 1-piperazinyl, 4-methyl-1-piperazinyl, or 4-morpholinyl, which comprises displacing the fluoro substituent from a 2-amino-6-fluorobenzonitrile derivative of the formulae:
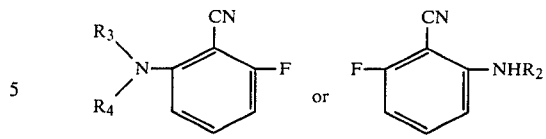
with an amine of the formulae:
H$_2$NR$_2$ or NHR$_3$R$_4$, respectively, by reaction at a temperature of about 75° C. to about 200° C.
* * * * *